US010656138B2

(12) United States Patent
Lei

(10) Patent No.: US 10,656,138 B2
(45) Date of Patent: May 19, 2020

(54) TEST BARREL FOR PLACING TEST PAPER CARD

(71) Applicant: Zhejiang Orient Gene Biotech Co., Ltd, Anji, Huzhou (CN)

(72) Inventor: Siyu Lei, Anji (CN)

(73) Assignee: Zhejiang Orient Gene Biotech Co., Ltd., Anji Huzhou (CN)

( * ) Notice: Subject to any disclaimer, the term of this patent is extended or adjusted under 35 U.S.C. 154(b) by 296 days.

(21) Appl. No.: 15/475,687

(22) Filed: Mar. 31, 2017

(65) Prior Publication Data

US 2018/0011078 A1 Jan. 11, 2018

(30) Foreign Application Priority Data

Jul. 8, 2016 (CN) .................... 2016 2 0718552 U

(51) Int. Cl.
*B01L 3/00* (2006.01)
*G01N 33/487* (2006.01)

(52) U.S. Cl.
CPC ........ *G01N 33/48778* (2013.01); *B01L 3/502* (2013.01); *B01L 3/523* (2013.01); *B01L 2200/16* (2013.01); *B01L 2300/042* (2013.01); *B01L 2300/0663* (2013.01); *B01L 2300/0809* (2013.01); *B01L 2300/0832* (2013.01); *B01L 2300/0848* (2013.01); *B01L 2300/123* (2013.01)

(58) Field of Classification Search
CPC ........ B01L 3/50; B01L 3/502; B01L 3/50825; B01L 2300/04; B01L 2300/041; G01N 21/01; G01N 33/00; B65D 41/0471
See application file for complete search history.

(56) References Cited

U.S. PATENT DOCUMENTS 5,403,551 A * 4/1995 Galloway ............ A61B 10/007
422/417
6,277,646 B1 * 8/2001 Guirguis ............ A61B 10/007
422/417

* cited by examiner

*Primary Examiner* — Jill A Warden
*Assistant Examiner* — Dwayne K Handy
(74) *Attorney, Agent, or Firm* — Lathrop GPM LLP

(57) ABSTRACT

The present invention provides a test barrel for placing a test paper card. The test barrel comprises a barrel body and a barrel lid; wherein the barrel body comprises a place reminding board arranged on the barrel body; and the barrel lid comprises an elastic piece arranged on the barrel lid and mating with the place reminding board. The test barrel for placing a test paper card according to the present invention is simple in structure and convenient in operation, and greatly reduces time for test. In addition, a place reminding structure is arranged on the test barrel, which facilitates use of the test barrel for the user and achieves sealing reminding. Further, the test result is accurate, the reusage rate is high, and cleaning is convenient.

5 Claims, 3 Drawing Sheets

TEST BARREL FOR PLACING TEST PAPER CARD

CROSS-REFERENCE TO RELATED APPLICATIONS

This application claims the priority and benefit of Chinese Nat'l Patent App. Ser. No. 201620718552.0, filed Jul. 8, 2016.

STATEMENT REGARDING FEDERALLY SPONSORED RESEARCH OR DEVELOPMENT

Not applicable.

THE NAMES OF THE PARTIES TO A JOINT RESEARCH AGREEMENT

Not applicable.

REFERENCE TO AN APPENDIX SUBMITTED ON A COMPACT DISC AND AN INCORPORATED BY REFERENCE OF THE MATERIAL ON THE COMPACT DISC

Not applicable.

STATEMENT REGARDING PRIOR DISCLOSURES BY THE INVENTOR OR A JOINT INVENTOR

Reserved for a later date, if necessary

BACKGROUND OF THE INVENTION

Field of Invention

The present invention relates to the technical field of testing, and in particular, relates to a test barrel for placing a test paper card.

Background of the Invention

In medical diagnosis field, body fluid testing is very common. Body fluid samples are tested by using devices having reagent strips to detect whether the analyzed substances are contained in the samples, which is disclosed or described in many prior arts. These reagent strips generally comprise a reagent region and a test region, wherein the reagent region may comprise a sample receiving area and a marker area. The test region comprises an area displaying a test result and a test result comparison area in the downstream of the test region. Typically, the test result displaying area may be strip-shaped, and color changes are indicated in the test result displaying area to indicate whether the sample contains the analyzed substance. At present, many test paper cards may be available in the market. Using such test paper cards, the same test liquid may be subjected to different test items at the same time, thereby saving the test time. However, the design of the test paper card is generally very simple, and is inconvenient to secure. Therefore, a container for placing the test paper card is desired. Patent with authorization publication No. CN203287379 (2013 Nov. 13) has disclosed a test board for placing a test paper strip. The test board, although implementing multiple tests of the same sample at the same time, has a complicated structure, and the mounting of the test paper is complicated, which overall does not reduce the time for operation, and cleaning upon testing is inconvenient.

SUMMARY OF THE INVENTION

In view of the above problem, the present invention is intended to provide a test barrel for placing a test paper card, which is simple in structure and convenient in operation, and greatly reduces time the for test. In addition, a place reminding structure is arranged on the test barrel, which facilitates use of the test barrel for the user and achieves sealing reminding. Further, the test result is accurate, the reusage rate is high, and cleaning is convenient.

The above objective of the present invention is implemented by employing the following technical solutions:

A test barrel for placing a test paper card is provided, comprising a barrel body and a barrel lid; wherein the barrel body comprises a place reminding board arranged on the barrel body; and the barrel lid comprises an elastic piece arranged on the barrel lid and mating with the place reminding board.

In this technical solution, the place reminding board and the elastic piece are arranged on the test barrel, such that the user is capable of accurately knowing whether the barrel lid is property turned during use of the test barrel, to thereby achieve an optimal sealing effect. In addition, no damage would be caused to the test barrel due to forces applied by individuals, and thus the service life of the test barrel is ensured to the greatest extent and the usage rate is increased.

Preferably, the barrel body is configured to be a hollow cuboid structure, wherein a top end of the cuboid structure extends perpendicularly upwards to define a cylindrical barrel mouth, a periphery of the barrel mouth is provided with threads connecting to the barrel lid, the cuboid structure is internally provided with a securing member for securing a test paper card, and the securing member is configured to a cylindrical bump. The shape of the securing member is determined according to the test paper card. Any structure capable of securing the test paper card may be used as an alternative of the structure in this technical solution and applied to the test barrel.

Preferably, the place reminding board is a strip-shaped bump arranged on the barrel body, wherein a side of the bump that is in contact with the elastic piece is configured to a flat surface. In this technical solution, the strip-shaped bump is selected to act as the place reminding board because the manufacture thereof is convenient and is simply formed. Therefore, any structure that may act as the place reminding board may be an alternative of the structure in this technical solution and applied to the test barrel. The bump is attached to one side of the elastic piece to increase the reminding sound, and facilitates hearing by the human ears.

Preferably, the barrel lid is configured to a cylindrical structure having an opening at a bottom end thereof, and two symmetric ends of the cylindrical barrel lid extend to define a force bearing portion having the same height as the cylindrical structure, wherein a side face of the force bearing portion is provided with bands, and an inner wall of the cylindrical barrel lid having an opening at the button end thereof is provided with threads mating with the barrel mouth. The force bearing portion is arranged such that the user conveniently turns the barrel lid, and the bands arranged on the side face of the force bearing portion are intended to increase the friction such that the turning of the barrel lid is more convenient and less labor consuming.

Preferably, the force bearing portion is configured to a hollow structure, the elastic piece is arranged in the force bearing portion, and the elastic piece is configured to an elastic strip-shaped tab, wherein a side of the tab that is in contact with the place reminding board is configured to a flat surface. In this technical solution, the strip-shaped bump is selected to act as the elastic piece because the manufacture thereof is convenient and is simply formed. Therefore, any structure that may act as the elastic piece may be an alternative of the structure in this technical solution and applied to the test barrel. The bump is attached to one side of the place reminding board to increase the reminding sound, and facilitates hearing by the human ears and operation thereof.

Preferably, the test paper card comprises a card body, securing portions arranged on left and right ends of the card body and configured to secure the card body to the securing member, more than one test paper trough arranged between the securing portions, and a liquid running portion arranged between the test paper troughs.

Preferably, the test paper trough comprises a retaining portion, an observation portion arranged below the retaining portion and configured to observe the test paper, a press portion arranged below the observation portion and configured to press the test paper, and a test portion arranged below the press portion and configured to further secure the test paper and contact a test liquid.

In this technical solution, the test paper card is divided into four parts, the securing portion may be configured to secure the entire device, such that the entire card device is stably secured in the test liquid; a plurality of test paper troughs are arranged, such that the test personnel may simultaneously carry out tests in the same test liquid, preventing contamination or waste of the test liquid due to tests for multiple times. In addition, in this technical solution, a liquid running portion is arranged, such that the card body is secured in the test device, and when the test liquid is added, no siphonage occurs, which prevents the case where the test result is inaccurate because the test paper is frequently in contact with the test liquid or the test liquid is not tested according to the test portions specified in the test paper. Furthermore, in this technical solution, the test paper card may be integrally formed via injection molding and may also be formed via lamination, and therefore the manufacture process is simple and convenient, the manufacture cost is low, and the test effect is good.

Preferably, the securing portion is configured to a hollow structure and configured to be connected and secured to the securing portion. The securing portion is configured to a hollow structure to conveniently secure the card to the securing member, such that the test paper is capable of stably testing a test liquid in the test barrel, thereby avoiding swing of the test barrel and increasing the accuracy of the test result.

Preferably, the width of the observation portion is greater than the width of the retaining portion, the height of the press portion is less than the height of the observation portion or the retaining portion, and the height of the press portion is between 0.8 mm and 1.5 mm. The configurations of the height and width of the observation portion are intended to more conveniently observe the test progresses in the test paper, and the inner space of the observation portion is configured to be greater than the liquid running portion, which also reduces the probability of siphonage and improves the test accuracy. The configuration of the height of the press portion is intended to, in one aspect, better hold the test paper and prevent the test paper from offsetting, and, in another aspect, to prevent the test liquid from flowing to the observation portion from the press portion and thus contaminating the test paper in the observation portion, such that the test liquid is only tested by the test paper at the test portion, thereby improving the test accuracy.

Preferably, the test portion comprises a raising portion connected to the press portion and a test part connected to the raising portion and configured to contact the test liquid, wherein the height of the test part is equal to or greater than the height of the press portion. The raising portion is configured to act as a transition between the test part and the press portion, to provide a batter liquid contact area for the test portion of the test paper and improve the test accuracy.

In conclusion, the present invention has the following beneficial effects:

1. The present invention provides a test barrel for placing a test paper card, which is simple in structure and convenient in operation, and greatly reduces time the for test. In addition, a place reminding structure is arranged on the test barrel, which facilitates use of the test barrel for the user and achieves sealing reminding. Further, the test result is accurate, the reusage rate is high, and cleaning is convenient.

2. The present invention provides a test barrel for placing a test paper card, such that the user is capable of accurately knowing whether the barrel lid is property turned during use of the test barrel, to thereby achieve an optimal sealing effect. In addition, no damage would be caused to the test barrel due to forces applied by individuals, and thus the service life of the test barrel is ensured to the greatest extent and the usage rate is increased.

BRIEF DESCRIPTION OF THE SEVERAL VIEWS OF THE DRAWINGS

Other objectives of the disclosure will become apparent to those skilled in the art once the invention has been shown and described. The manner in which these objectives and other desirable characteristics can be obtained is explained in the following description and attached figures in which:

FIG. 2 is a schematic structural view of the present invention; and,

Figure 1:
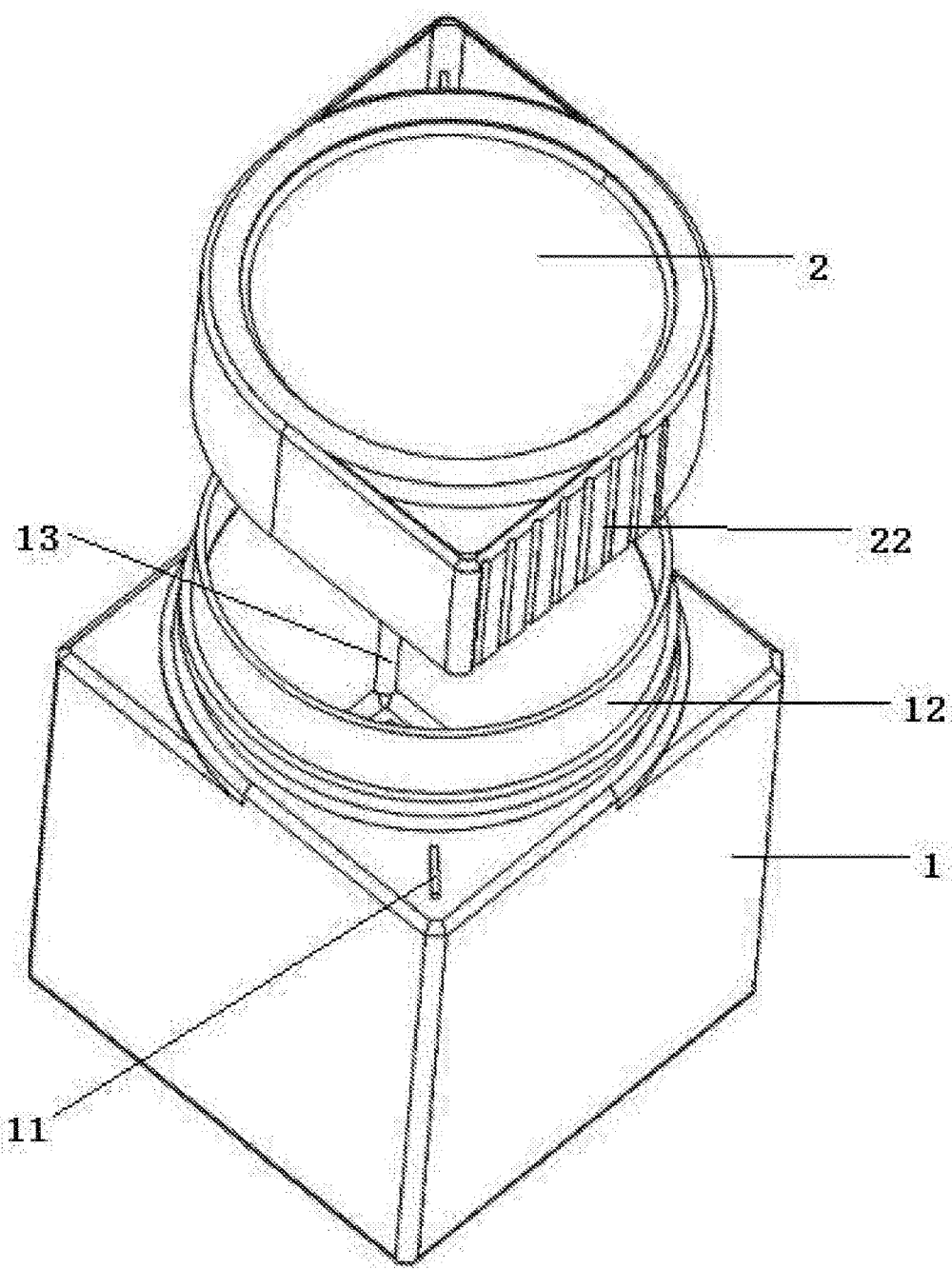
FIG. 1 is a schematic structural view of the present invention.

In the drawings, 1 denotes a barrel body, 2 denotes a barrel lid, 3 denotes a test paper card, 11 denotes a place reminding board, 12 denotes a barrel mouth, 13 denotes a securing member, 21 denotes an elastic piece, 22 denotes a force bearing portion, 31 denotes a card body, 32 denotes a securing portion, 33 denotes a test paper trough, 34 denotes a liquid running portion, 331 denotes a retaining portion, 332 denotes an observation portion, 333 denotes a press portion, 334 denotes a test portion, 3341 denotes a raising portion, and 3342 denotes a test part.

It is to be noted, however, that the appended figures illustrate only typical embodiments of this invention and are therefore not to be considered limiting of its scope, for the invention may admit to other equally effective embodiments that will be appreciated by those reasonably skilled in the relevant arts. Also, figures are not necessarily made to scale but are representative.

DETAILED DESCRIPTION OF PREFERRED EMBODIMENTS

The present invention is further described with reference to the accompanying drawings.

The specific embodiments herein are merely intended to interpret the present invention, instead of limiting the present invention. Upon reading the specification herein, a person skilled in the art would make modifications of no innovative contributions to the embodiments, and these modifications shall be protected by the patent right as long as they fall within the scope defined by the claims of the present invention.

Figure 2:
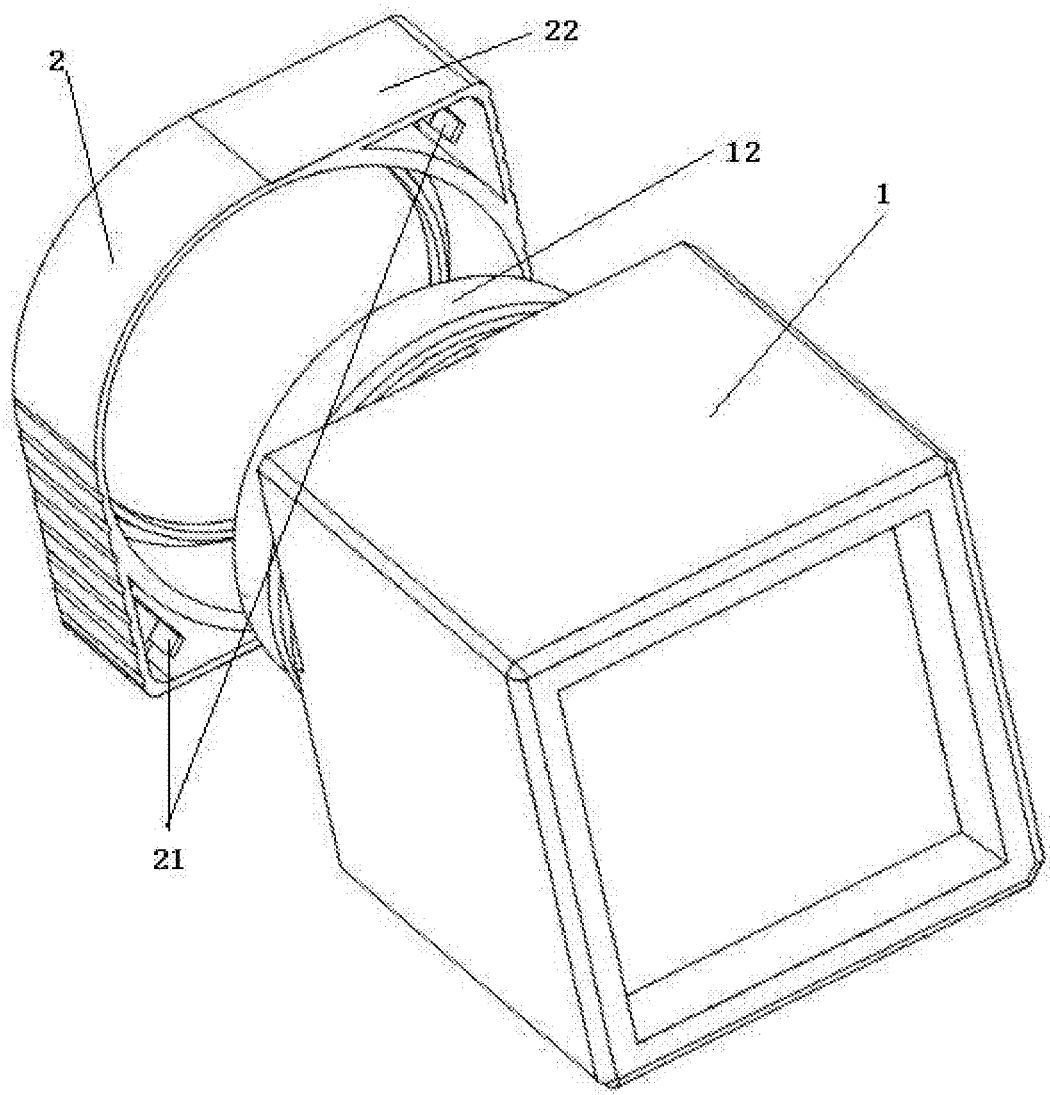
FIG. 2 is the exploded view of this utility model.

As illustrated in FIG. 1 and FIG. 2, a test barrel for placing a test paper card is provided. The test barrel comprises a barrel body 1 and a barrel lid 2; wherein the barrel body 1 comprises a reminding board 11 arranged on the barrel body 1; and the barrel lid 2 comprises an elastic piece 21 arranged on the barrel lid 2 and mating with the place reminding board 11.

In this technical solution, the place reminding board 11 and the elastic piece 21 are arranged on the test barrel, such that the user is capable of accurately knowing whether the barrel lid 2 is property turned during use of the test barrel, to thereby achieve an optimal sealing effect. In addition, no damage would be caused to the test barrel due to forces applied by individuals, and thus the service life of the test barrel is ensured to the greatest extent and the usage rate is increased.

The barrel body 1 is configured to be a hollow cuboid structure, wherein a top end of the cuboid structure extends perpendicularly upwards to define a cylindrical barrel mouth 12, a periphery of the barrel mouth 12 is provided with threads connecting to the barrel lid 2, the cuboid structure is internally provided with a securing member 13 for securing a test paper card 3, and the securing member 13 is configured to a cylindrical bump. The shape of the securing member is determined according to the test paper card. Any structure capable of securing the test paper card may be used as an alternative of the structure in this technical solution and applied to the test barrel.

The place reminding board 11 is a strip-shaped bump arranged on the barrel body 1, wherein a side of the bump that is in contact with the elastic piece 21 is configured to a flat surface. In this technical solution, a strip-shaped bump is selected to act as a place reminding board because the manufacture thereof is convenient and is simply formed. Therefore, any structure that may act as the place reminding board may be an alternative of the structure in this technical solution and applied to the test barrel. The bump is attached to one side of the elastic piece to increase the reminding sound, and facilitates hearing by the human ears.

The barrel lid 2 is configured to a cylindrical structure having an opening at a bottom end thereof, and two symmetric ends of the cylindrical barrel lid 2 extend to define a force bearing portion 22 having the same height as the cylindrical structure, wherein a side face of the force bearing portion 22 is provided with bands, and an inner wall of the cylindrical barrel lid 2 having an opening at the button end thereof is provided with threads mating with the barrel mouth 12. The force bearing portion 22 is arranged such that the user conveniently turns the barrel lid 2, and the bands arranged on the side face of the force bearing portion 22 are intended to increase the friction such that the turning of the barrel lid 2 is more convenient and less labor consuming.

The force bearing portion 22 is configured to a hollow structure, and the elastic piece 21 is arranged in the force bearing portion, and the elastic piece 21 is configured to an elastic strip-shaped tab, wherein a side of the tab that is in contact with the place reminding board 11 is configured to a flat surface. In this technical solution, the strip-shaped bump is selected to act as the elastic piece because the manufacture thereof is convenient and is simply formed. Therefore, any structure that may act as the elastic piece may be an alternative of the structure in this technical solution and applied to the test barrel. The bump is attached to one side of the place reminding board to increase the reminding sound, and facilitates hearing by the human ears and operation thereof.

Figure 3:
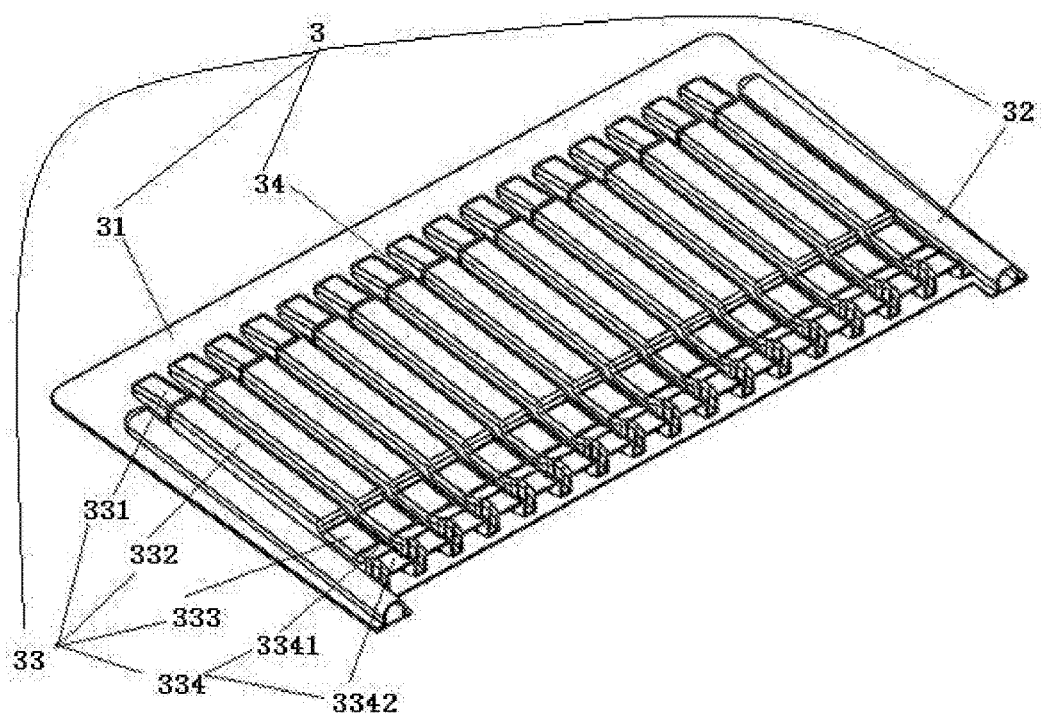
FIG. 3 is a schematic structural view of a test paper card according to the present invention.

As illustrated in FIG. 3, the test paper card 3 comprises a card body 31, securing portions 32 arranged on left and right ends of the card body 31 and configured to secure the card body 31 to the securing member 13, more than one test paper trough 33 arranged between the securing portions 32, and a liquid running portion 34 arranged between the test paper troughs 33.

The test paper trough 33 comprises a retaining portion 331, an observation portion 332 arranged below the retaining portion 331 and configured to observe the test paper, a press portion 333 arranged below the observation portion 332 and configured to press the test paper, and a test portion 334 arranged below the press portion 333 and configured to further secure the test paper and contact a test liquid.

In this technical solution, the test paper card 3 is divided into four parts, the securing portion may be configured to secure the entire device, such that the entire card device is stably secured in the test liquid; a plurality of test paper troughs are arranged, such that the test personnel may simultaneously carry out tests in the same test liquid, preventing contamination or waste of the test liquid due to tests for multiple times. In addition, in this technical solution, a liquid running portion is arranged, such that the card body is secured in the test device, and when the test liquid is added, no siphonage occurs, which prevents the case where the test result is inaccurate because the test paper is frequently in contact with the test liquid or the test liquid is not tested according to the test portions specified in the test paper. Furthermore, in this technical solution, the test paper card may be integrally formed via injection molding and may also be formed via lamination, and therefore the manufacture process is simple and convenient, the manufacture cost is low, and the test effect is good.

The securing portion 32 is configured to a hollow structure and configured to be connected and secured to the securing portion 313. The securing portion 32 is configured to a hollow structure to conveniently secure the card to the securing member 313, such that the test paper is capable of stably testing a test liquid in the test barrel, thereby avoiding swing of the test barrel and increasing the accuracy of the test result.

The width of the observation portion 332 is greater than the width of the retaining portion 331, the height of the press portion 333 is less than the height of the observation portion 332 or the retaining portion 331, and the height of the press portion 333 is between 0.8 mm and 1.5 mm. The configurations of the height and width of the observation portion are intended to more conveniently observe the test progresses in the test paper, and the inner space of the observation portion is configured to be greater than the liquid running portion, which also reduces the probability of siphonage and improves the test accuracy. The configuration of the height of the press portion is intended to, in one aspect, better hold the test paper and prevent the test paper from offsetting, and, in another aspect, to prevent the test liquid from flowing to the observation portion from the press portion and thus contaminating the test paper in the observation portion, such that the test liquid is only tested by the test paper at the test portion, thereby improving the test accuracy.

The test portion 334 comprises a raising portion 3341 connected to the press portion 333 and a test part 3342 connected to the raising portion 3341 and configured to contact the test liquid, wherein the height of the test part 3342 is equal to or greater than the height of the press portion 333. The raising portion is configured to act as a transition between the test part and the press portion, to provide a batter liquid contact area for the test portion of the test paper and improve the test accuracy.

Although the method and apparatus is described above in terms of various exemplary embodiments and implementations, it should be understood that the various features, aspects and functionality described in one or more of the individual embodiments are not limited in their applicability to the particular embodiment with which they are described, but instead might be applied, alone or in various combinations, to one or more of the other embodiments of the disclosed method and apparatus, whether or not such embodiments are described and whether or not such features are presented as being a part of a described embodiment. Thus the breadth and scope of the claimed invention should not be limited by any of the above-described embodiments.

Terms and phrases used in this document, and variations thereof, unless otherwise expressly stated, should be construed as open-ended as opposed to limiting. As examples of the foregoing: the term "including" should be read as meaning "including, without limitation" or the like, the term "example" is used to provide exemplary instances of the item in discussion, not an exhaustive or limiting list thereof, the terms "a" or "an" should be read as meaning "at least one," "one or more," or the like, and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that might be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases might be absent. The use of the term "assembly" does not imply that the components or functionality described or claimed as part of the module are all configured in a common package. Indeed, any or all of the various components of a module, whether control logic or other components, might be combined in a single package or separately maintained and might further be distributed across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives might be implemented without confinement to the illustrated examples. For example, block diagrams and their accompanying description should not be construed as mandating a particular architecture or configuration.

All original claims submitted with this specification are incorporated by reference in their entirety as if fully set forth herein.

What is claimed is:

1. A test barrel for placing a test paper card, comprising:
   a barrel body (1) comprising a barrel mouth with threads thereon and two place reminding boards (11) symmetrically arranged on the barrel body (1) separately, and wherein each of the two place reminding boards comprises a flat surface, and wherein a strip-shaped bump is arranged on the flat surface of the place reminding board (11);
   wherein the barrel body (1) is configured to be a hollow cuboid structure, wherein a top end of the cuboid structure extends perpendicularly upwards to define a cylindrical barrel mouth (12), a periphery of the barrel mouth (12) is provided with threads connecting to a barrel lid (2), the cuboid structure is internally provided with a securing member (13) for securing the test paper card (3), and the securing member (13) is configured to be a cylindrical bump;
   the barrel lid (2) comprising a cylindrical structure having an opening at a bottom end thereof; two symmetric ends of the cylindrical barrel lid (2) extends to define two symmetrical force bearing portions (22) having the same height as the cylindrical structure, wherein a side face of the force bearing portion (22) is provided with bands, and an inner wall of the cylindrical barrel lid (2) is provided with threads mating with the threads of the barrel mouth (12); and wherein each of the two force bearing portions is a hollow structure and each of the hollow structures has an elastic strip-shaped tab (21) therein so that when the lid secures on the mouth of the barrel body, each of the two elastic strip-shaped tabs contacts each of the two strip-shaped bumps respectively as to produce a reminding sound to achieve an optimal sealing effect; and
   a test paper card (3) comprising a card body (31), securing portions (32) arranged on left and right ends of the card body (31) and configured to secure the card body (31) to the securing member (13), more than one test paper trough (33) arranged between the securing portions (32), and a liquid running portion (34) arranged between the test paper troughs (33); said test paper card further comprising a retaining portion, an observation portion for observing the test paper, a press portion for pressing the test paper and a test portion for securing the test paper.

2. The test barrel for placing a test paper card according to claim 1,
   wherein a side of the bump that is in contact with the elastic piece (21) is configured to a flat surface.

3. The test barrel for placing a test paper card according to claim 1, wherein the securing portion (32) is a hollow structure and configured to be connected and secured to the securing portion (313).

4. The test barrel for placing a test paper card according to claim 1, wherein
   the width of the observation portion (332) is greater than the width of the retaining portion (331), the height of the press portion (333) is less than the height of the observation portion (332) or the retaining portion (331), and the height of the press portion (333) is between 0.8 mm and 1.5 mm.

5. The test barrel for placing a test paper card according to claim 4, wherein
   the test portion (334) comprises a raising portion (3341) connected to the press portion (333) and a test part (3342) connected to the raising portion (3341) and configured to contact the test liquid, wherein the height of the test part (3342) is equal to or greater than the height of the press portion (333).

* * * * *